US00PP14882P2

(12) United States Plant Patent
Olbricht

(10) Patent No.: US PP14,882 P2
(45) Date of Patent: Jun. 8, 2004

(54) VARIETY OF PELARGONIUM PLANT NAMED 'PACBICOLOR'

(50) Latin Name: *Pelargonium crispum*
Varietal Denomination: Pacbicolor

(75) Inventor: Klaus Olbricht, Dresden (DE)

(73) Assignee: Elsner pac Jungpflanzen Dresden, Dresden (DE)

( * ) Notice: Subject to any disclaimer, the term of this patent is extended or adjusted under 35 U.S.C. 154(b) by 0 days.

(21) Appl. No.: 10/456,282

(22) Filed: Jun. 6, 2003

(51) Int. Cl.[7] ..... A01H 5/00
(52) U.S. Cl. ..... Plt./324
(58) Field of Search ..... Plt./324

*Primary Examiner*—Kent Bell
(74) *Attorney, Agent, or Firm*—Webb Ziesenheim Logsdon Orkin & Hanson, P.C.

(57) ABSTRACT

A new and distinct flowering Pelargonium plant with abundant red-purple colored flowers.

1 Drawing Sheet

Botanical classification: *Pelargonium crispum.*
Varietal denomination: 'Pacbicolor'.

BACKGROUND OF THE INVENTION

The present invention comprises a new and distinct cultivar of *Pelargonium crispum* hybrid known by the varietal name 'Pacbicolor'. The new variety was discovered in a selected breeding program in Dresden, Germany. The new variety is the result of combination breeding from a collection of proprietary breeding plants. The flower habit and size of the new variety are similar to its parents but with different flower color. The new variety was first asexually reproduced in November 2000 by cuttings in Dresden, Germany. The new variety was grown in a warm greenhouse in January; then moved outside in February; then transferred to baskets in May. The new variety has been trial and field tested in Dresden and has been found to retain its distinctive characteristics and remain true to type through successive propagations.

DESCRIPTION OF THE DRAWINGS

The accompanying photographic drawing illustrates the new variety, with the color being as nearly true as is possible with color illustrations of this type.

DESCRIPTION OF THE PLANT

Figure 1:
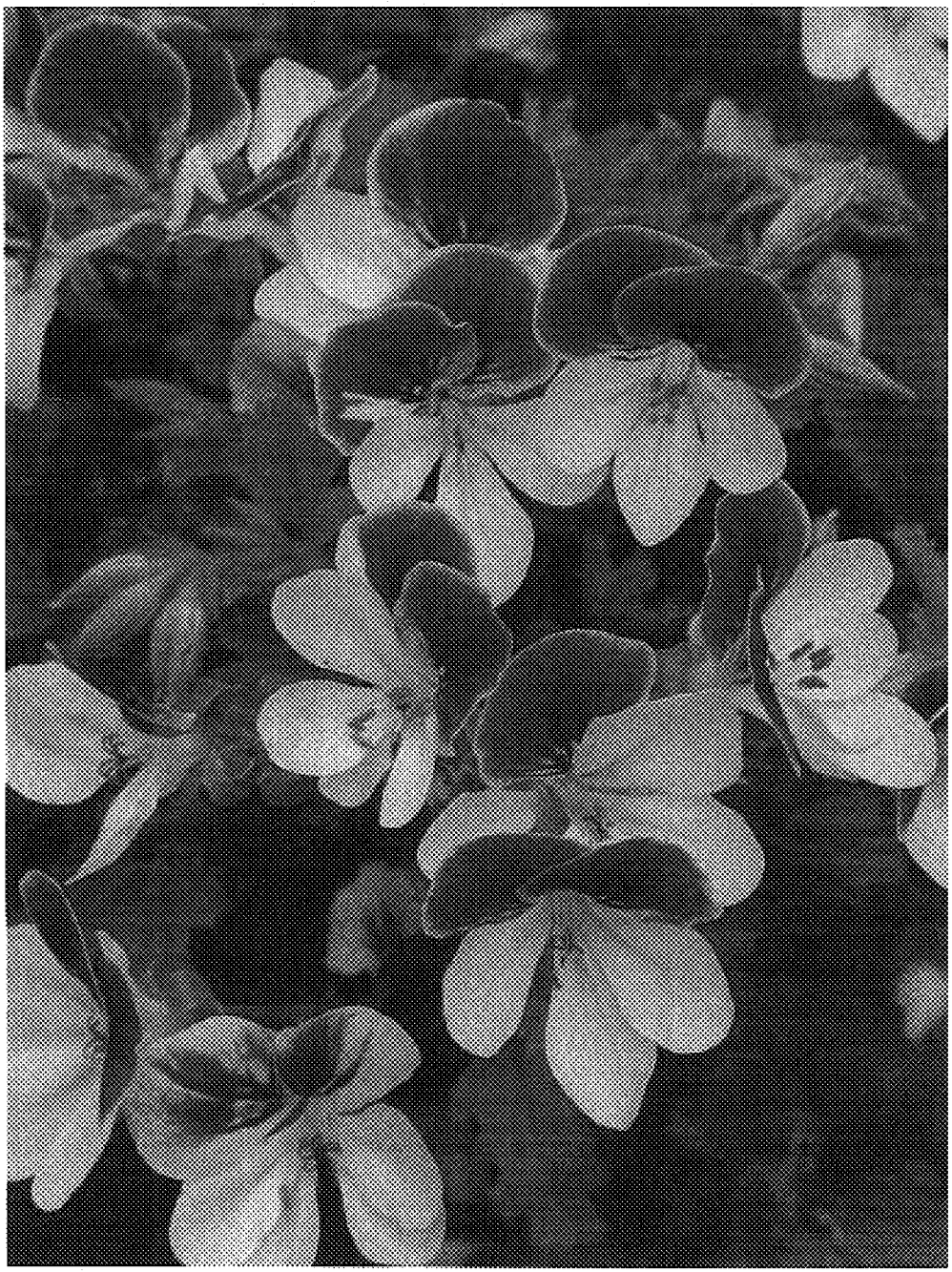

The following detailed description sets forth the characteristics of the new cultivar. The data which defines these characteristics were collected by asexual reproductions by carried out in a warm greenhouse in Dresden, Germany. Plants were about 9 months old when described. The color readings were taken on a plant indoors under natural light. Color references are primarily to The R.H.S. Colour Chart of The Royal Horticultural Society of London.

PLANT

Form: Cascading; mounded.
Height: 10–12 cm from soil to top of foliage; 15 cm from soil to top of umbels.
Diameter: 50 cm.
Growth: Erect, well-branched.
Strength: Does not require artificial support; self-standing.

Foliage: No zonation.
Time to develop roots: 3.5 weeks.
Description of roots: White; adventive.
Leaves:
- *Size.*—Length: 1.8–2.0 cm. Width: 1.8–2.0 cm.
- *Shape.*—Overall: Transverse, maple leaf like. Base: Open. Apex: Pointed.
- *Margin.*—Bi-serrate.
- *Texture.*—Hairy.
- *Color.*—Upper surface: 138A. Lower surface: 144A.
- *Ribs and veins.*—Venation: Net-like. Color: 143B.

Petioles:
- *Color.*—143B.
- *Length.*—0.5–1.0 cm.
- *Diameter.*—2 mm.

Stem:
- *Length.*—Average 10 cm.
- *Color.*—143B.
- *Internode length.*—Average 1 cm.
- *Lateral branch length.*—Average 5 cm.

THE BUD (Measurements Taken Just Prior to Opening)

Shape:
- *Cluster.*—Spindle.
- *Individual bud.*—Elliptic.

Size:
- *Cluster.*—Approximately 1.7×1.7 cm.
- *Individual bud.*—Approximately 0.4×1.0 cm.

Color: 143A.

INFLORESCENCE

Blooming habit: Umbels.
Size:
- *Width.*—5 cm.
- *Depth.*—2.5 cm.

Borne: Umbel; flowers on pedicel; pedicel on peduncle.
Number of flowers per umbel: 2–3.
Lastingness of the bloom on the plant: 5 to 8 days.

Flowers:

*Form.*—Zygomorphic.

*Size.*—Diameter: 2.2–2.5 cm. Depth: Approximately 1.5 cm.

*Petals.*—Number per flower: 5. Color: Two Upper Petals: Upper surface: 67A with 69C margin and 61A stripes. Lower surface: 75A. Three Lower Petals: Upper surface: 69C. Lower surface: 69D. Shape: Overall: Round to oval. Apex: Round; not pointed. Base: Pointed. Size: Length: 2.0–2.5 cm. Width: 1.0–1.7 cm. Margin: Entire. Texture: Smooth. Tonality: Nice bi-colored flowers.

Sepals:

*Number per bloom.*—5.

*Color.*—Upper surface: 143A. Lower surface: 143B.

*Shape.*—Overall: Pointed; narrow. Apex: Pointed. Base: Wider and not pointed. Margin: Entire.

*Size.*—Length: Approximately 1 cm. Width: Approximately 0.4 cm.

Pedicel:

*Length.*—Approximately 1.5 cm.

*Color.*—143B.

Peduncle:

*Length.*—2–2.5 cm.

*Color.*—143B.

Disease/pest resistance: No susceptibility to diseases or pests has been noted to date.

Flowering season: Summer.

REPRODUCTIVE ORGANS

Stamens:

*Anthers.*—0.1–0.2 cm long.

*Filaments.*—Length: Approximately 1 cm. Color: 65D.

*Pollen.*—Uncountable.

Pistils:

*Number.*—One.

*Length.*—Approximately 1 cm.

*Stigma color.*—59A.

*Style.*—Length: Approximately 0.4 cm. Color: 70C.

*Ovaries.*—Superior; hairy; 0.2 cm; Greenish in color.

Seeds: Rarely present.

*Amount.*—5 per flower maximum.

*Size.*—3 mm.

*Color.*—Brown.

GENERAL CHARACTERISTICS

'Pacbicolor' has the following general characteristics.

1. Compact growth; cascading with age.
2. Able to cultivate in small pots.
3. Beautiful flowers.
4. Extremely high cutting yield.
5. Abundant flowers.

I claim:

1. A new and distinct variety of Pelargonium plant substantially as shown and described.

* * * * *